United States Patent
Anderson et al.

(10) Patent No.: US 10,006,096 B2
(45) Date of Patent: Jun. 26, 2018

(54) METHODS FOR DETECTION OF ANTI-CYTOMEGALOVIRUS NEUTRALIZING ANTIBODIES

(71) Applicant: VARIATION BIOTECHNOLOGIES, INC., Gatineau (CA)

(72) Inventors: David E. Anderson, Boston, MA (US); Jasminka Bozic, Ottawa (CA); Barthelemy Ontsouka, Montreal (CA)

(73) Assignee: Variation Biotechnologies Inc., Ottawa (CA)

( * ) Notice: Subject to any disclaimer, the term of this patent is extended or adjusted under 35 U.S.C. 154(b) by 1 day.

(21) Appl. No.: 14/387,870

(22) PCT Filed: Mar. 27, 2013

(86) PCT No.: PCT/IB2013/001021
§ 371 (c)(1),
(2) Date: Sep. 25, 2014

(87) PCT Pub. No.: WO2013/144722
PCT Pub. Date: Oct. 3, 2013

(65) Prior Publication Data
US 2015/0044668 A1 Feb. 12, 2015

Related U.S. Application Data

(60) Provisional application No. 61/616,204, filed on Mar. 27, 2012.

(51) Int. Cl.
*C12Q 1/70* (2006.01)
*G01N 33/50* (2006.01)
*G01N 33/68* (2006.01)
*A61K 39/12* (2006.01)
*A61K 39/00* (2006.01)

(52) U.S. Cl.
CPC ............. *C12Q 1/70* (2013.01); *A61K 39/12* (2013.01); *G01N 33/5044* (2013.01); *G01N 33/6854* (2013.01); *A61K 2039/5258* (2013.01); *A61K 2039/55505* (2013.01); *A61K 2039/70* (2013.01); *C12N 2710/16134* (2013.01); *G01N 2333/045* (2013.01); *G01N 2469/20* (2013.01)

(58) Field of Classification Search
None
See application file for complete search history.

(56) References Cited

U.S. PATENT DOCUMENTS

| | | | | |
|---|---|---|---|---|
| 5,248,768 A * | 9/1993 | Lussenhop | ............ | C07K 16/088 424/230.1 |
| 6,569,616 B1 * | 5/2003 | Compton | ............ | C07K 14/005 424/184.1 |
| 6,849,409 B2 * | 2/2005 | Schubart | ............ | A61K 31/00 435/235.1 |
| 2010/0267583 A1 | 10/2010 | Azizi | | |
| 2010/0285059 A1 * | 11/2010 | Shenk | ............ | A61K 39/245 424/204.1 |

FOREIGN PATENT DOCUMENTS

| CN | 1686541 A | 10/2005 |
|---|---|---|
| CN | 101522213 A | 9/2009 |
| CN | 101820906 A | 9/2010 |
| JP | H06-222062 A | 8/1994 |
| JP | 2002-537830 A | 11/2002 |
| WO | WO-00/53729 A2 | 9/2000 |
| WO | WO-2008/025095 A1 | 3/2008 |
| WO | WO-2013/068847 A2 | 5/2013 |

OTHER PUBLICATIONS

Wang et al. Quantitative analysis of neutralizing antibody response to human cytomegalovirus in natural infection. Vaccine. Nov. 8, 2011;29(48):9075-80.*
Cui et al. Antibody inhibition of human cytomegalovirus spread in epithelial cell cultures. J Virol Methods. Sep. 2013;192(1-2):44-50.*
Kirchmeier et al. Enveloped virus-like particle expression of human cytomegalovirus glycoprotein B antigen induces antibodies with potent and broad neutralizing activity. Clin Vaccine Immunol. Feb. 2014;21(2):174-80.*
Cui et al. Bacterial artificial chromosome clones of viruses comprising the towne cytomegalovirus vaccine. J Biomed Biotechnol. 2012;2012:428498.*
Spiller et al. Neutralization of cytomegalovirus virions: the role of complement. J Infect Dis. Aug. 1997;176(2):339-47. (Year: 1997).*
Auewarakul, P. et al., Application of HIV-1-green fluorescent protein (GFP) reporter viruses in neutralizing antibody assays, Asian Pacific Journal of Allergy and Immunology, 19(2): 139-144 (2001).
Bickerstaff, A.A. et al., A flow cytometry-based method for detecting antibody responses to murine cytomegalovirus infection, Journal of Virological Methods, 142 (1-2): 50-58 (2007).
Earl, P.L. et al., Development and use of a vaccinia virus neutralization assay based on flow cytometric detection of green fluorescent protein, Journal of Virology, 77(19): 10684-10688 (2003).
International Search Report for PCT/IB2013/001021, 3 pages (dated Oct. 4, 2013).
Rimmelzwaan, G.U. et al., Use of GFP-expressing influenza viruses for the detection of influenza virus A/H5N1 neutralizing antibodies, Vaccine, 29(18): 3424-3430 (2011).

(Continued)

*Primary Examiner* — Michelle S Horning
(74) *Attorney, Agent, or Firm* — Choate, Hall & Stewart LLP; Charles E. Lyon; Rolando Medina

(57) ABSTRACT

The present disclosure provides methods useful for determining levels of HCMV infection in host cells and, by extension, determining levels of neutralizing antibodies present in a sample. The present disclosure encompasses the recognition that HCMV viruses that have a fluorescent moiety permit detection of viral infection (e.g., by assessing fluorescence in cells after contacting the host cell with the virus). In some embodiments, levels of HCMV infection are determined by fluorescence detection where the virus has been preincubated with a test sample (e.g., a serum sample) from a subject. In some embodiments, the subject has been administered a candidate HCMV vaccine.

21 Claims, 5 Drawing Sheets

(56) References Cited

OTHER PUBLICATIONS

Saccoccio, F.M. et al., Peptides from cytomegalovirus UL130 and UL131 proteins induce high titer antibodies that block viral entry into mucosal epithelial cells, Vaccine, 29: 2705-2711 (2011).
Straschewski, S. et al., Human Cytomegaloviruses Expressing Yellow Fluorescent Fusion Proteins-Characterization and Use in Antiviral Screening, PLoS One, 5(2): e9174 (2010).
Wang, Z. et al., Development of an efficient fluorescence-based microneutralization assay using recombinant human cytomegalovirus strains expressing green fluorescent protein, Journal of Virological Methods, 120(2): 207-215 (2004).
Written Opinion for PCT/IB2013/001021, 5 pages (dated Oct. 4, 2013).
Sampaio, K.L. et al., Human Cytomegalovirus Labeled with Green Fluorescent Protein for Live Analysis of Intracellular Particle Movements, Journal of Virology, 79(5): 2754-2767 (2005).
Cheng Wei, Li Chunde ed. Immunophysiology, published by Shanghai Scientific & Technical Publishers, 178 (Aug. 1993). No Known English Language Copy Available.
Abai, A. M. et al., Novel Microneutralization Assay for HCMV Using Automated Data Collection Analysis, J. Immunol. Methods. 322(1-2):82-93 (2007).
Gerna, G. et al., Human cytomegalovirus serum neutralizing antibodies block virus infection of endothelial/epithelial cells, but not fibroblasts, early during primary infection, Journal of General Virology, 89:853-865 (2008).

\* cited by examiner

POTENT & SUSTAINED IMMUNITY OF BIVALENT GB VLPS IN RABBITS AFTER A SINGLE IMMUNIZATION

METHODS FOR DETECTION OF ANTI-CYTOMEGALOVIRUS NEUTRALIZING ANTIBODIES

CROSS REFERENCE TO RELATED APPLICATIONS

This application claims the benefit of U.S. provisional application Ser. No. 61/616,204, filed on Mar. 27, 2012, the contents of which are herein incorporated by reference in their entirety.

BACKGROUND

Human cytomegalovirus (HCMV), a β-herpesvirus, is a ubiquitously occurring pathogen. In an immunocompetent person, HCMV infection is normally unnoticed, having at most mild and nonspecific symptoms. By contrast, certain risk groups, for example in immunosuppressed patients such as AIDS patients or transplant recipients, and after prenatal infection, HCMV infection has serious manifestations (Staras S A et al., 2006 Clin Infect Dis 43(9):1143-51; Hebart H et al., 2004 Hum Immunol 65(5):432-6; Rowshani A T et al., 2005 Transplantation 79(4):381-6). Existing therapies include the use of immunoglobulins and anti-viral agents such as ganciclovir and its derivatives, which are most effective when used prophylactically or very early during infection in at risk populations. However, existing therapies are characterized by significant toxicity and limited efficacy, especially for late-onset disease (Boeckh M., 2004 Pediatr Transplant 8(Suppl. 5):19-27; Limaye A P., 2004 Transplantation 78(9):1390-6), and they have not had an impact on congenital HCMV disease. Development of an effective vaccine to protect against HCMV disease is recognized as an important public health priority (Arvin A M et al., 2004 Clin Infect Dis 39(2):233-9).

In vitro assays are important tools to evaluate candidate vaccines for their ability to interfere with HCMV infection. For example, neutralization assays have been developed to study immune responses in infected individuals as well as to assess vaccine immunogen candidates in both clinical and preclinical trials. In the case of HCMV, antigen binding ELISAs can measure antibodies specific for HCMV antigens; however, only an assay in which neutralization of viral entry into cells is measured can establish and quantify the biological activity of HCMV antigen-specific antibodies (Abai et al., 2007 J Immunol Methods 332(1-2):82-93). Typically, in such neutralization assays for HCMV, the degree to which neutralizing antibodies reduce HCMV infection of cells in the assay is determined by quantification of nuclei of infected cells based on expression of one or more viral proteins in the cell. Such analyses can be time consuming and difficult to employ in high throughput applications. There remains a need in the art for improved methods of screening potential HCMV vaccine candidates for neutralizing antibody induction.

SUMMARY

Among other things, the present disclosure provides methods useful for determining levels of HCMV infection in host cells and, by extension, determining levels of neutralizing antibodies present in a sample. The present disclosure encompasses the recognition that HCMV viruses that have a fluorescent moiety permit detection of viral infection (e.g., by assessing fluorescence in cells after contacting the host cell with the virus). In some embodiments, levels of HCMV infection are determined by fluorescence detection where the virus has been preincubated with a test sample (e.g., a serum sample) from a subject. In some embodiments, the subject has been administered a candidate HCMV vaccine.

Other features, objects, and advantages of the present disclosure are apparent in the detailed description that follows. It should be understood, however, that the detailed description, while indicating embodiments of the present disclosure, is given by way of illustration only, not limitation. Various changes and modifications within the scope of the disclosure will become apparent to those skilled in the art from the detailed description.

BRIEF DESCRIPTION OF THE DRAWINGS

The drawings are for illustration purposes only, not for limitation.

DEFINITIONS

Figure 1:
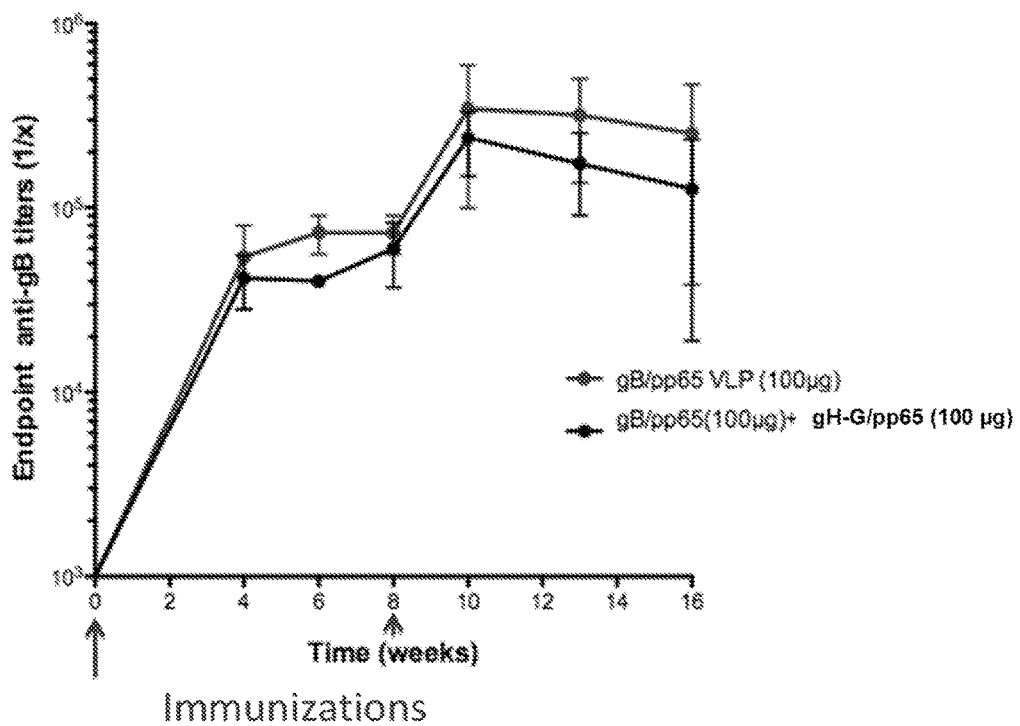
FIG. 1 depicts exemplary ELISA anti-gB antibody titers after immunization with bivalent gB virus-like particles (VLPs) (gB/pp65 and gB/pp65+gH-G/pp65). A potent and sustained immunity is induced by bivalent gB VLPs in rabbits after a single immunization.

In order for the present disclosure to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or aminoterminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antigen: As used herein, the term "antigen" refers to a substance containing one or more epitopes (either linear, conformational or both) that are recognized by antibodies. In certain embodiments, an antigen is or comprises a virus or a viral polypeptide. In some embodiments, the term "antigen" refers to a subunit antigen (i.e., an antigen which is separate and discrete from a whole virus with which the antigen is associated in nature; e.g., an antigen which is associated with a virus-like particle). Alternatively or additionally, in some embodiments, the term "antigen" refers to killed, attenuated or inactivated viruses. In certain embodiments, an antigen is an "immunogen."

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease, disorder or condition (e.g., HCMV infection). The term "prevention" refers to a delay of onset of a disease, disorder or condition. Prevention may be considered complete when onset of a disease, disorder or condition has been delayed for a predefined period of time.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Fluorescence: As used herein, the term fluorescence refers to a moiety that luminesces. Typically fluorescent moieties contain electrons which can absorb electromagnetic energy at one wavelength and emit electromagnetic energy at a second wavelength. Some proteins or small molecules in cells are naturally fluorescent (e.g., NADH, tryptophan, endogenous chlorophyll, phycoerythrin, or green fluorescent protein (GFP)). It will be appreciated that various mutants of fluorescent proteins have been engineered and may be used in accordance with the present disclosure, such as EGFP, blue fluorescent protein (EBFP, EBFP2, Azurite, mKalamal), cyan fluorescent protein (ECFP, Cerulean, CyPet), yellow fluorescent protein (YFP, Citrine, Venus, YPet), redox sensitive GFP (roGFP), and monomeric GFP, among others. GFP and other fluorescent proteins can be expressed exogenously in cells alone or as a fusion protein. This approach permits fluorescent proteins to be used as reporters for any number of biological events, such as subcellular localization and expression patterns.

Alternatively or additionally, specific or general proteins, nucleic acids, lipids or small molecules can be labeled with an extrinsic fluorophore, a fluorescent dye which can be a small molecule, protein or quantum dot. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G;

Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson—; Calcium Green; Calcium Green-1 Ca.sup.2+ Dye; Calcium Green-2 Ca.sup.2+; Calcium Green-5N Ca.sup.2+; Calcium Green-C18 Ca.sup.2+; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (Di1C18(5)); DIDS; Dihydrohodamine 123 (DHR); Di1 (Di1C18(3)); I Dinitrophenol; DiO (DiOC18 (3)); DiR; DiR (Di1C18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-1 PRO-3; Primuline; Procion Yellow; Propidium lodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl)quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

Fusion protein: As used herein, the term "fusion protein" generally refers to a polypeptide including at least two segments, each of which shows a high degree of amino acid identity to a peptide moiety that (1) occurs in nature, and/or (2) represents a functional domain of a polypeptide. Typically, a polypeptide containing at least two such segments is considered to be a fusion protein if the two segments are moieties that (1) are not included in nature in the same peptide, and/or (2) have not previously been linked to one another in a single polypeptide, and/or (3) have been linked to one another through action of the hand of man.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein—coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

High-throughput: As used herein, the term "high-throughput" refers broadly to investigations with a large number of assays such that formatting of each individual sample, minimizing preparation steps and complications, and measuring of the assay results either in parallel or in rapid succession become important. High-throughput tests generally do not include manual, one-at-a-time assays, such as assays by a single individual in which the preparation, execution, measurement, and data collection for one assay are all completed before the assay on the next agent is done. High-throughput typically includes, for example, any assays in which a batch of samples (e.g., 24, 96, 384 or more test samples) are prepared and measured. Formatting the tests in such test samples is meant to accelerate the assay process by enabling measurement in parallel or in rapid succession, such as with the assistance of automation.

Immunogenic: As used herein, the term "immunogenic" means capable of producing an immune response in a host animal against a non-host entity (e.g., an HCMV antigen). In certain embodiments, this immune response forms the basis of the protective immunity elicited by a vaccine against a specific infectious organism (e.g., an HCMV).

Immune response: As used herein, the term "immune response" refers to a response elicited in an animal. An immune response may refer to cellular immunity, humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum). In certain embodiments, an immunogenic composition may induce virus-neutralizing antibodies or a neutralizing antibody response.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein.

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult) suffering from a disease, for example, HCMV infection. In some embodiments, the subject is at risk for HCMV infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject has been exposed to HCMV infection. In some embodiments, the subject is a human.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Linker: As used herein, the term "linker" refers to, e.g., in a fusion protein, an amino acid sequence of an appropriate length other than that appearing at a particular position in the natural protein and is generally designed to be flexible and/or to interpose a structure, such as an a-helix, between two protein moieties. In general, a linker allows two or more domains of a fusion protein to retain 50%, 55%, 60%, 65%, 70%, 75%, 80%, 85%, 90%, 95% or more of the biological activity of each of the domains. A linker may also referred to as a spacer.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present disclosure. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present disclosure is specifically directed to "unmodified nucleic acids," meaning nucleic acids (e.g., polynucleotides and residues, including nucleotides and/or nucleosides) that have not been chemically modified in order to facilitate or achieve delivery.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, or condition (e.g., HCMV infection) has been diagnosed with and/or exhibits one or more symptoms of the disease, disorder, or condition.

Susceptible to: An individual who is "susceptible to" a disease, disorder, or condition (e.g., HCMV infection) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to HCMV).

Symptoms are reduced: According to the present disclosure, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. It is not intended that the present disclosure be limited only to cases where the symptoms are eliminated. The present disclosure specifically contemplates treatment such that one or more symptoms is/are reduced (and the condition of the subject is thereby "improved"), albeit not completely eliminated.

Therapeutically effective amount: As used herein, the term "therapeutically effective amount" refers to an amount sufficient to confer a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular immunogenic composition, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific immunogenic composition employed; the duration of the treatment; and like factors as is well known in the medical arts.

Treatment: As used herein, the term "treatment" (also "treat" or "treating") refers to any administration of an immunogenic composition that partially or completely alleviates, ameliorates, relieves, inhibits, delays onset of, reduces severity of and/or reduces incidence of one or more symptoms or features of a particular disease, disorder, and/or condition (e.g., HCMV infection) or the predisposition toward the disease. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, the term "treating" refers to the vaccination of a patient.

Tropism: As used herein, the terms "tropism" or "host tropism" or "cell tropism" in the context of viruses and other pathogens generally refer to the ability of the virus or pathogen to infect a particular cell type. Tropism may refer to a way in which the virus or pathogen has evolved to preferentially target specific host species or specific cell types within those species. For example, HCMV can typically infect a remarkably broad cell range within its host, including parenchymal cells, connective tissue cells of virtually any organ and various hematopoietic cell types. Epithelial cells, endothelial cells, fibroblasts and smooth muscle cells are predominant targets for virus replication. However, the tropism for various cells varies greatly among different HCMV strains, e.g., from alterations within the UL128-131 gene locus. In some embodiments, an HCMV strain is able to infect fibroblasts, but not epithelial and/or endothelial cells. In some embodiments, an HCMV strain is able to infect fibroblasts, epithelial cells and endothelial cells.

Vaccination: As used herein, the term "vaccination" refers to the administration of a composition intended to generate an immune response, for example to a disease-causing agent (e.g., HCMV). For the purposes of the present disclosure, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Vector: As used herein, "vector" refers to a nucleic acid molecule capable of transporting another nucleic acid to which it is associated. In some embodiments, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF CERTAIN EMBODIMENTS

Among other things, the present disclosure provides methods useful for determining levels of HCMV infection in host cells and, by extension, determining levels of neutralizing antibodies present in a sample. The present disclosure encompasses the recognition that HCMV viruses that have a fluorescent moiety permit detection of viral infection (e.g., by assessing fluorescence in cells after contacting the host cell with the virus). In some embodiments, levels of HCMV infection are determined by fluorescence detection where the virus has been preincubated with a test sample (e.g., a serum sample) from a subject. In some embodiments, the subject has been administered a candidate HCMV vaccine.

I. HCMV Infection and Vaccines

Human cytomegalovirus (HCMV), a β-herpesvirus, is a ubiquitously occurring pathogen. In general, entry of herpesviruses into cells is a complex process initiated by adsorption and receptor binding and followed by fusion of the virus envelope with a cell membrane. Fusion generally occurs at either the plasma membrane or an endosomal membrane. HCMV infects multiple cell types in vivo, including epithelial cells, endothelial cells and fibroblasts (Plachter B et al., 1996 Adv Virus Res 46:195-261). It fuses with the plasma membranes of fibroblasts (Compton T et al., 1992 Virology 191:387-395), but enters retinal pigmented epithelial cells and umbilical vein endothelial cells via endocytosis (Bodaghi B et al., 1999 J Immunol 162:957-964; Ryckman B J et al., 2006 J Virol 80:710-722). The mechanism by which herpesviruses choose their route of entry remains unclear. It is generally assumed that entry pathways are mainly determined by the host cell, but there is evidence for tropic roles of virion glycoproteins (Wang X et al., 1998 J Virol 72:5552-5558). HCMV encodes two gH/gL complexes: gH/gL/gO and gH/gL/UL128/UL130/UL131. The gO-containing complex is sufficient for fibroblast infection, whereas the pUL128/UL130/UL131-containing complex is important for HCMV infection of endothelial and epithelial cells. As used herein, the terms "tropism" or "host tropism" or "cell tropism" in the context of viruses and other pathogens generally refer to the ability of the virus or pathogen to infect a particular cell type. Tropism may refer to a way in which the virus or pathogen has evolved to preferentially target specific host species or specific cell types within those species. In some embodiments, an HCMV strain is able to infect fibroblasts, but not epithelial and/or endothelial cells. In some embodiments, an HCMV strain is able to infect fibroblasts, epithelial cells and endothelial cells.

HCMV infects 50-85% of adults by 40 years of age (Gershon A A et al., 1997 in *Viral Infections of Humans*, 4$^{th}$ edition, New York; Plenum Press: 229-251). Most healthy individuals who acquire HCMV after birth develop few, if any, symptoms. However, HCMV disease is the cause of significant morbidity and mortality in immunocompromised individuals, such as recipients of hematopoietic cell transplants (HCT) and solid-organ transplants (SOT) (Pass R F 2001 Cytomegalovirus. In Fields Virology. 4$^{th}$ edition, Philadelphia; Lippincott Williams & Wilkens: 2675-2705). In SOT or HCT populations, HCMV disease can occur either from new infection transmitted from the donor organ or HCT, or can recur as a result of reactivation of latent virus in the recipient. In HIV-infected individuals, HCMV infection accelerates progression to AIDS and death, despite availability of antiretroviral therapy (Deayton J R et al., 2004 Lancet 363:2116-2121). In addition in the US, HCMV is the most common intrauterine infection and causes congenital abnormalities resulting in death or severe birth defects, including deafness and mental retardation, in approximately 8,000 infants each year (Stagon S et al., 1986 JAMA 256:1904-1908).

Immune responses which control HCMV are incompletely understood. By analogy to other human herpesviruses it can be assumed that both cellular and humoral immune responses play an important role (Kohl S 1992 Current topics in Microbiology and Immunology 179:75-88). For murine CMV it was shown that either a cytotoxic T cell response or the passive transfer of neutralizing antibodies is sufficient to protect against a lethal challenge (Rapp M et al., 1993 Multidisciplinary Approach to Understanding Cytomegalovirus Disease 327-332; Reddehase M J et al., 198 J Virology 61:3102-3108).

Control of HCMV in immunocompromised persons is primarily associated with cellular immune responses; both $CD8^+$ and $CD4^+$ T lymphocytes appear to be important for protection against CMV disease (Gamadia L E et al., 2003 Blood 101:2686-2692; Cobbold M et al., 2005 J Exp Med 202:379-386). The cellular immune response to CMV includes $CD4^+$ helper T-lymphocyte and $CD8^+$ Cytotoxic T-lymphocyte responses to a number of antigens, found in the viral tegument, the region of the viral particle between the envelope and capsid. A recent study of CMV-specific $CD4^+$ and $CD8^+$ T cells from healthy donors used overlapping peptides from a series of CMV open reading frames to identify antigens recognized after CMV infection (Sylwester A W et al., 2005 J Exp Med 202:673-685). The CMV tegument phosphoprotein 65 (pp65) and surface glycoprotein gB were the antigens most frequently recognized by $CD4^+$ T cells, and pp65 was also one of the antigens most frequently recognized by $CD8^+$ T cells.

In contrast to the transplant setting, the maternal humoral immune response against the virus seems to be important in preventing HCMV disease in the newborn. Antibodies to surface glycoproteins, especially gB, appear to be critical for protection against the maternal-fetal transfer of HCMV (Fowler K B et al., 2003 JAMA 289:1008-1011). Moreover, in an earlier vaccination study it was shown that protection from re-infection is correlated with neutralizing antibodies (Adler S P et al., 1995 J Infectious Diseases 171:26-32). The humoral immune response to HCMV is dominated by responses to viral envelope glycoproteins present in the outer envelope of the virus particle (e.g., gB and gH).

In the case of HCMV, direct evaluation of immunological effector functions is difficult since the virus is strictly species specific and no animal model system is available. However, murine CMV and guinea pig CMV have been used to evaluate vaccine strategies in these host species.

A CMV vaccine that induces both protective T cell and neutralizing antibody responses has the potential to prevent infection or ameliorate CMV disease due to congenital infection or transplantation.

The first live, attenuated HCMV vaccine candidate tested in humans was based on the laboratory-adapted AD169 strain. Subsequent trials with another laboratory-adapted clinical isolate, the Towne strain, confirmed that live attenuated vaccines could elicit neutralizing antibodies, as well as CD4+ and CD8+ T lymphocyte responses. The efficacy of the Towne vaccine was assessed in a series of studies in renal transplant recipients. Although the Towne vaccine did provide a protective impact on HCMV disease it failed to prevent HCMV infection after transplantation (Plotkin S A et al., 1984 Lancet 1:528-530). Towne vaccine was also evaluated in a placebo-controlled study of seronegative mothers who had children attending group daycare where it failed to prevent these women from acquiring infection from their HCMV-infected children (Adler S P et al., 1995 J Infectious Diseases 171:26-32). An interpretation of these studies was that the Towne vaccine was overattenuated. To explore this possibility a series of genetic recombinants in which regions of the unattenuated "Toledo" strain of CMV were substituted for the corresponding regions of the Towne genome, resulting in the construction of Towne/Toledo "chimeras" that contain some, but not all, of the mutations that contribute to the Towne vaccine attenuation (Heineman T C et al. 2006 J Infect Disease 193:1350-1360). The safety and tolerability of four Towne/Toledo "chimeras" is being tested in a Phase I trial. Long-term safety concerns about the potential risk of establishing a latent HCMV infection have hindered the further development of live, attenuated vaccines.

The leading subunit CMV vaccine candidate is based on the envelope glycoprotein, gB, (purified recombinant gB vaccine is manufactured by Sanofi-Pasteur Vaccines) due to this protein's ability to elicit high-titer, virus-neutralizing antibody responses during natural infection. The recombinant gB vaccine elicits neutralizing antibody responses and has an excellent safety profile, however, it excludes other glycoprotein targets of neutralizing antibody response and more importantly T-lymphocyte targets. The vaccine requires MF59 adjuvant to optimize immunogenicity. In the most recent trial, this vaccine provided an overall 50% efficacy for prevention of CMV infection in a Phase 2 clinical trial in young women (Pass R F et al., 2009 N Engl J Med 360:1191-1199). Other viral proteins being evaluated as subunit vaccine candidates include pp65 and IE1, both of which elicit T-cell responses.

DNA vaccines elicit robust cellular and humoral immune responses in animals and are well suited to specificity and precision in vaccine design. DNA vaccines have been developed for CMV and have focused on gB, IE1 and pp65 proteins as the candidate target immunogens. A bivalent CMV DNA vaccine candidate (Wloch M K, 2008 J Infectious Diseases 297:1634-1642), using plasmid DNA encoding pp65 and gB and a trivalent vaccine candidate (Jacobson M A, 2009 Vaccine 27:1540-1548) that also includes a third plasmid encoding the IE1 gene product have been developed by Vical Vaccines (U.S. Pat. No. 7,410,795). The trivalent DNA vaccine alone had minimal immunogenicity irrespective of route of administration. However the CMV DNA vaccine did appear to safely prime for a memory response to CMV antigens observed after administration of a live, attenuated CMV (Towne).

In a vectored vaccine approach, the gene product of interest is expressed in the context of a non-replicating (usually viral) carrier. One example of this is a canarypox vector called ALVAC developed by Virogenetics and Sanofi-Pasteur Vaccines, which is an attenuated poxvirus that replicates abortively in mammalian cells. ALVAC expressing CMV gB and ALVAC expressing pp65 (U.S. Pat. No. 6,267,965) have been tested in clinical trials. ALVAC-CMV (gB) did not induce neutralizing antibodies but did prime for higher neutralizing antibody titers after subsequent infection with the Towne strain CMV (Adler S P et al., 1999 J Infectious Diseases 180:843-846), although it did not appear to boost neutralizing antibody titers after subsequent immunization with gB subunit/MF59 vaccine (Bernstein D I et al., 2002 J Infectious Diseases 185:686-690). A canarypox vector expressing pp65, ALVAC-CMV(pp64), induced long-lasting CTL responses in all originally seronegative volunteers, at frequencies comparable to naturally seropositive individuals (Berencsi K et al., 2001 J Infectious Diseases 183:1171-1179). Another approach used to express gB as a vectored vaccine is the use of an alphavirus replicon system by AlphaVax Inc (U.S. Pat. No. 7,419,674). This approach involves a propagation-defective single-cycle RNA replicon vector system derived from an attenuated strain of an alphavirus, Venezuelan Equine Encephalitis (VEE) virus, to produce virus-like replicon particles (VRPs) expressing pp65, IE1 or gB protein (Berstein et al., 2010 Vaccine 28:484-493). A two component alphavirus replicon vaccine was used to express the three CMV proteins as a soluble form of CMV gB (Towne strain) and a pp65/IE1 fusion protein (Reap E A et al., 2007 Vaccine 25:7441-7449) was found to be safe and induced high levels of neutralizing antibody and polyfunctional CD4+ and CD8+ antigen-specific T cell responses. The Geometric Mean Titre (GMT) for the high dose group was about half the GMT in 12 naturally infected, CMV seropositive individuals tested in the assay.

A candidate for vaccination against HCMV currently in preclinical development is the "dense body" vaccine. Dense bodies (DBs) are enveloped, replication-defective particles formed during the replication of CMVs in cell culture. They contain both envelope glycoproteins and large quantities of pp65 protein. DBs are non-infectious and immunogenic but incapable of establishing latent HCMV infection in the vaccine recipient. DBs have been shown to be capable of inducing virus neutralizing antibodies and T-cell responses in mice in the absence of viral gene expression (Pepperl S et al., 2000 J Virol 74:6132-6146, PCT Publication No. WO 00/53729 and U.S. Pat. No. 6,713,070).

Additional candidates contemplated for vaccination against HCMV are virus like particles (VLPs). Retroviruses are enveloped RNA viruses that belong to the family Retroviridae. After infection of a host cell by a retrovirus, RNA is transcribed into DNA via the enzyme reverse transcriptase. DNA is then incorporated into the host cell's genome by an integrase enzyme and thereafter replicates as part of the host cell's DNA. The Retroviridae family includes the following genus *Alpharetrovirus, Betaretrovirus, Gammearetrovirus, Deltaretrovirus, Epsilonretrovirus, Lentivirus* and *Spumavirus*. The hosts for this family of retroviruses generally are vertebrates. Retroviruses produce an infectious virion containing a spherical nucleocapsid (the viral genome in complex with viral structural proteins) surrounded by a lipid bilayer derived from the host cell membrane.

Retroviral vectors can be used to generate enveloped virions that are infectious and either replication-competent or replication-defective. Replication-competent infectious retroviral vectors contain all of the necessary genes for virion synthesis and continue to propagate themselves once infection of the host cell occurs. Replication-defective infectious retroviral vectors do not spread after the initial infection. This is accomplished by replacement of most of the coding regions of the retrovirus with genes or nucleotide sequences to be transferred; so that the vector is incapable of making proteins required for additional rounds of replication.

Alternatively or additionally, retroviral vectors can be used to generate virus-like particles (VLPs) that lack a retrovirus-derived genome and are both non-infectious and non-replicating. Because of VLPs advantageous properties, VLPs may be utilized as an antigen delivery system. Furthermore, because VLPs are non-infectious, they can be administered safely as an immunogenic composition (e.g., a vaccine). VLPs are generally structurally similar to enveloped virions described above, but lack a retrovirus-derived genome, making it unlikely that viral replication will occur. Expression of capsid proteins (e.g., Gag) of some viruses (e.g., murine leukemia viruses, such as Moloney Murine leukemia virus (MMLV)) leads to self-assembly into particles similar to the corresponding native virus, which particles are free of viral genetic material.

A wide variety of VLPs have been prepared. For example, VLPs including single or multiple capsid proteins either with or without envelope proteins and/or surface glycoproteins have been prepared. In some cases, VLPs are non-enveloped and assemble by expression of just one major capsid protein, as shown for VLPs prepared from hepadnaviruses (e.g., Engerix™, GSK and Recombivax HB™, Merck), papillomaviruses (e.g., Cervarix™, GSK and Gardasil™, Merck), paroviruses, or polyomaviruses. In some embodiments, VLPs are enveloped and can comprise multiple antigenic proteins found in the corresponding native virus. VLPs typically resemble their corresponding native virus and can be multivalent particulate structures. In some embodiments, antigenic proteins may be presented internally within the VLP, as a component of the VLP structure, and/or on the surface of the VLP. In some embodiments, presentation of an antigen in the context of a VLP is advantageous for induction of neutralizing antibodies against the antigen as compared to other forms of antigen presentation, e.g., soluble antigens not associated with a VLP. Neutralizing antibodies most often recognize tertiary or quaternary structures; this often requires presenting antigenic proteins, like envelope glycoproteins, in their native viral conformation. Alternatively or additionally, VLPs may be useful for presenting antigens in a context which induces cellular immunity (e.g., T cell response). In some embodiments, use of antigen combinations in VLP systems can generate improved immune response.

II. Detectable HCMV

As described above, among other things, the present disclosure provides methods for determining levels of HCMV infection in host cells and, by extension, determining levels of neutralizing antibodies present in a sample. The present disclosure encompasses the recognition that HCMV viruses that have a fluorescent moiety permit detection of viral infection (e.g., by assessing fluorescence in cells after contacting the host cell with the virus). In some embodiments, levels of HCMV infection are determined by fluorescence detection where the virus has been preincubated with a test sample (e.g., a serum sample) from a subject. In some embodiments, the subject has been administered a candidate HCMV vaccine.

Provided methods utilize an HCMV virus that includes a fluorescent moiety. Any HCMV virus capable of infecting a host cell described herein can be engineered to include a fluorescent moiety. In some embodiments, to infect fibroblasts, an HCMV virus that includes all or a portion of a gH/gL/gO complex can be engineered to include a fluorescent moiety. In some embodiments, to infect endothelial cells and/or epithelial cells, an HCMV virus that includes all or a portion of a gH/gL/UL128/UL130/UL131 complex can be engineered to include a fluorescent moiety. Modified HCMV strains that are amenable to fluorescent detection are known in the art and may be used in accordance with the present disclosure. For example, UL32-EGFP-HCMV-TB40 is an in vitro recombination of HCMV strain TB40 with a plasmid carrying the TB40 UL32 gene fused to GFP (ATCC; VR-1578). The UL32-EGFP-HCMV-TB40 recombinant strain gives rise to a recombinant HCMV virus with GFP fused to the C terminus of the tegument phosphoprotein pp150, the product of the UL32 gene (Sampaio et al., 2005 Journal of Virology 79(5):2754). Because GFP is associated with a viral structural protein, virus particles fluoresce green under appropriate illumination. The UL32-EGFP-HCMV-TB40 strain has been demonstrated to have tropism for fibroblast cells (Sampaio et al., 2005 Journal of Virology 79(5):2754). An additional HCMV strain that is amenable to fluorescent detection is HB15-t178b, which contains the CMV strain AD169 genome and a GFP reporter cassette (Saccoccio et al., 2011 Vaccine 29(15):2705).

It is to be understood that the term fluorescence, as used herein, refers to a moiety that luminesces. Typically fluorescent moieties contain electrons which can absorb electromagnetic energy at one wavelength and emit electromagnetic energy at a second wavelength. Some proteins or small molecules in cells are naturally fluorescent (e.g., NADH, tryptophan, endogenous chlorophyll, phycoerythrin, or green fluorescent protein (GFP)). It will be appreciated that various mutants of fluorescent proteins have been engineered and may be used in accordance with the present disclosure, such as EGFP, blue fluorescent protein (e.g., EBFP, EBFP2, Azurite, mKalamal), cyan fluorescent protein (e.g., ECFP, Cerulean, CyPet), yellow fluorescent protein (e.g., YFP, Citrine, Venus, YPet), redox sensitive GFP (e.g., roGFP), and monomeric GFP, among others. GFP and other fluorescent proteins can be expressed exogenously in cells alone or as a fusion protein. This approach permits fluorescent proteins to be used as reporters for any number of biological events, such as subcellular localization and expression patterns.

Alternatively or additionally, specific or general proteins, nucleic acids, lipids or small molecules can be labeled with an extrinsic fluorophore, a fluorescent dye which can be a small molecule, protein or quantum dot. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor® 350; Alexa Fluor® 430; Alexa Fluor® 488; Alexa Fluor® 532; Alexa Fluor® 546; Alexa Fluor® 568; Alexa Fluor® 594; Alexa Fluor® 633; Alexa Fluor® 647; Alexa Fluor® 660; Alexa Fluor® 680; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green™; Calcium Green™-1 $Ca^{2+}$ Dye; Calcium Green™-2 $Ca^+$; Calcium Green™-5N $Ca^{2+}$; Calcium Green™-C18 $Ca^{2+}$; Calcium Orange™; Calcofluor White; Carboxy-X-rhodamine (5-ROX); Cascade Blue®; Cascade Yellow™; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (Di1C18(5)); DIDS; Dihydrorhodamine 123 (DHR); Di1 (Di1C18(3)); I Dinitrophenol; DiO (DiOC18(3)); DiR; DiR (Di1C18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM® 1-43; FM® 4-64; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-lndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green® Oregon Green® 488; Oregon Green® 500; Oregon Green® 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; P0-1 PRO-3; Primuline; Procion Yellow; Propidium lodid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl)quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red®; Texas Red®-X conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

III. Infection Assays

Determination of infectious titer of HCMV typically includes contacting a host cell that is susceptible to infection by HCMV with serial dilutions of the virus (e.g., HCMV that includes a fluorescent moiety), under conditions that allow cell infection in the absence of any test substance. The number of target cells expressing a reporter gene construct (e.g., a fluorescent moiety, e.g., GFP) may be determined (e.g., by flow cytometry) to calculate the infectious titer of the virus preparation.

To assess the presence and/or activity of neutralizing antibodies in serum of a subject to whom a candidate vaccine has been administered, the serum may be pre-incubated with HCMV (e.g., HCMV that includes a fluorescent moiety, e.g., GFP) for a period of time sufficient for neutralizing antibodies to reduce infectivity of the HCMV (e.g., at least 15 minutes, at least 30 minutes, at least 1 hour, at least 2 hours, or more). Serial dilutions of the preincubated mixture of serum and HCMV (e.g., HCMV that includes a fluorescent moiety) may then be used to contact a host cell that is susceptible to infection by HCMV under conditions that allow infection. A person of ordinary skill in the art will be able to determine appropriate dilutions of serum for infection assays. For example, in some embodiments, dilutions tested are 1:6, 1:12, 1:24, 1:48, 1:96, 1:192, or combinations thereof.

It will be appreciated that conditions that allow infection may vary depending on a variety of factors, including viral strain, host cell type, temperature, cell confluence, viral concentration, among others. One of ordinary skill in the art would be able to modify infection conditions appropriately. In some embodiments, infection conditions include incubation of the host cell with virus for at least 1 hour, at least 2 hours, at least 3 hours, at least 4 hours, at least 5 hours, at least 6 hours, at least 7 hours, at least 8 hours, or more. It will also be appreciated that monitoring for infection of cells may include visual cellular morphology assessment (e.g., for cellular swelling and rounding) and/or visual fluorescence assessment (e.g., detecting fluorescence on a device such as a fluorescence microscope). After infection, host cells may be collected (e.g., by washing and trypsinizing and/or scraping) and analyzed by fluorescent detection methods available in the art and described herein.

Any host cell susceptible to infection by HCMV can be used in the methods described herein. Exemplary host cells include, but are not limited to human fibroblast cells, such as human foreskin fibroblasts (HFF), and human epithelial cells such, as retinal pigmented epithelial cells (ARPE-19). Medium in which host cells are grown during the infection assay may vary with cell type. For example, in some embodiments, HFF infection medium includes MEM+5%

FBS+1% PenStrep. In some embodiments, APRE infection medium includes DMEM:F-12+1% FBS.

IV. Fluorescence Detection and Neutralizing Antibody Assessment

Fluorescence may be detected using any appropriate method, including, for example, flow cytometry analysis, fluorescent activated cell sorting, or flow microfluorometry. It will be appreciated that the sensitivity of fluorescence detection generally depends on the number of copies of the fluorescent entity in the detection system, the efficiency of the detection instrument, and the fluorescence brightness of the fluorescent entity relative to background fluorescence that arises from endogenous biological fluorescent entities in the sample and from non-specific association of the fluorescent entity with the sample. The brightness of the fluorescent entity, in turn, depends on the quantum efficiency of the fluorescent entity that produces the fluorescence signal and the light absorbing capability (quantified by the extinction coefficient) of the fluorescent entity.

It is to be understood that cells can be identified and/or isolated based on levels of surface and/or intracellular fluorescence using reporter molecules such as green fluorescent protein (GFP). Generally, a correlation between fluorescence intensity and protein production (e.g., viral infection and production) will be observed. For example, in some embodiments, high levels of fluorescence intensity in a host cell correlates with high level of viral infection of the host cell.

In some embodiments, cells are assessed for overall fluorescence level (e.g., irrespective of subcellular localization of the fluorescence). In some embodiments, cells are assessed for fluorescence level in a particular subcellular location (e.g., the nucleus) of the cell. In general, flow cytometry permits quantitative phenotyping of large numbers of cells, however, many flow cytometry applications do not include an ability to image cells as they are quantitated. In some embodiments, detection and quantitation of fluorescence of cells is sufficient for assessing infection. It will be appreciated that in some cases it is desirable to determine the localization of fluorescence within the cell. In some embodiments, flow cytometry analysis of cells may be combined with visual assessment of fluorescence. Dual analysis of fluorescence level and localization may be performed using multiple devices (e.g., flow cytometry and fluorescence microscopy) or on a single device. Such devices that permit fluorescence analysis and/or quantitation in conjunction with localization analysis are available in the art. For example, ImageStream$^X$ (Amnis®) quantifies both intensity and localization of fluorescence and permits imaging of more than 50,000 cells per minute.

Cell fluorescence levels may be quantitated by any appropriate method known in the art. Cell fluorescence levels may be compared to a reference level. In some embodiments, the reference level is a predetermined or historical reference level. In some embodiments, the reference level is obtained by side-by-side comparison with a reference sample (e.g., a positive and/or negative control).

The advent of screening and selection methods that use flow cytometry and cell sorting considerably increase the number of cells that can be screened. For example, several million cells can be screened in a short time, and subpopulations and single cells can be isolated from within mixed-cell populations even when they are present at frequencies as low as $10^{-6}$ within the population. It will be appreciated that one of the advantages of provided methods is that sample assessment can be achieved in a high-throughput manner. In some embodiments, provided methods increase throughput by 10%, 20%, 30%, 40%, 50%, 60%, 70%, or more as compared to known infection and/or neutralizing antibody detection methods (e.g., staining of viral proteins, fluorescence microscopy, ELISPOT, etc.). Provided methods may be performed in a multi-well plate format and are therefore particularly suitable for use in mid-to-high throughput screening. In some embodiments, the multi-well plates have 96 wells. In some embodiments, the multi-well plates have another number of wells, which include but is not limited to plates with 6, 12, 24, 384, 864 or 1536 wells. The terms "multi-well plate" and "microtiter plate" are used interchangeably.

In some embodiments, live cells are analyzed. In some embodiments, cells are fixed prior to analysis.

In some embodiments, the present disclosure provides methods for measuring anti-HCMV neutralizing antibodies by correlating fluorescence detection and/or viral infection of host cells. For example, an HCMV that includes a fluorescent moiety (e.g., GFP) may be preincubated with serum from a subject immunized with an HCMV candidate vaccine. Neutralizing antibodies present in the serum will reduce HCMV (e.g., HCMV that includes a fluorescent moiety) from infecting a host cell that is normally susceptible to infection by HCMV. The preincubated mixture including HCMV (e.g., HCMV that includes a fluorescent moiety) and serum can then be used to contact such a host cell and fluorescence levels of the host cell may be assessed. Based on fluorescence levels in the host cell, a level of infection of the host cell can be determined. Level of infection of the host cell generally is inversely related to the presence and amount neutralizing antibody in the serum, which in turn, correlates with efficacy of the candidate vaccine to elicit a therapeutic response (e.g., a protective immune response). For example, the more efficacious a candidate vaccine at inducing neutralizing antibodies in a subject, the more neutralizing antibodies will be present in the serum, in turn corresponding to a decrease in ability of an HCMV that includes a fluorescent moiety to infect a host cell after pre-incubation with the serum, further corresponding to a decrease in fluorescence detection in the host cell after contacting it with an HCMV that includes a fluorescent moiety. In some embodiments, methods of the disclosure further include selecting and/or identifying, based on a correlation described herein, a candidate vaccine (e.g., an HCMV candidate vaccine) as a vaccine that induces neutralizing antibodies.

EXAMPLES

The following examples describe some exemplary modes of making and practicing certain compositions that are described herein. It should be understood that these examples are for illustrative purposes only and are not meant to limit the scope of the compositions and methods described herein.

Example 1: Immunization of Rabbits with Virus-Like Particles

This Example describes exemplary immunization of rabbits with virus-like particles containing various recombinant HCMV antigens.

HEK 293T cells (ATCC, CRL-11268) were transiently transfected using calcium phosphate methods with expression plasmids encoding various recombinant HCMV antigens. Expression of various HCMV antigens by the HEK 293 cells was confirmed by flow cytometry. After 48 to 72 hours of transfection, supernatants containing the VLPs were harvested and filtered through 0.45 µm pore size membranes and further concentrated and purified by ultracentrifugation through a 20% sucrose cushion in a SW32 Beckman rotor (25,000 rpm, 2 hours, 4° C.). Pellets were resuspended in sterile endotoxin-free PBS (GIBCO) to obtain 500 times concentrated VLP stocks. Total protein was determined on an aliquot by a Bradford assay quantification kit (BioRad). Purified VLPs were stored at −80° C. until used.

Rabbits were immunized intramuscularly at t=0 and t=8 weeks with VLPs as shown in Table 1 below. Serum was collected at t=4, 6, 8, 10, 13 and 16 weeks.

TABLE 1

| Test Article # (n = 6/group) | Dose | Test Article Description |
|---|---|---|
| 1 | 100 µg | gB/pp65 bivalent VLPs |
| 6 | 100 µg/each | gB/pp65 bivalent VLPs + gH-G/pp65 bivalent VLPs (1:1 ratio) |

Enzyme-linked Immunosorbent Assay (ELISA) was performed to determine rabbit serum HCMV IgG content. FIG. 1 shows potent and sustained immunity in rabbits immunized with gB/pp65 bivalent VLPs (upper) and gB/pp65 bivalent VLPs+gH-G/pp65 bivalent VLPs (lower).

Example 2: Flow Cytometry-Based Neutralization Activity

This Example describes assessment of neutralizing antibody responses to HCMV in serum from immunized animals. The objectives of this Example included, but were not limited to: 1) confirming the immunogenicity of CMV clinical candidate components selected from other animal studies; 2) assessing dose and potential synergy and/or antagonism with administration routes (e.g., IM vs. IP administration); and 3) assessing immunological boosting and durability of immunity.

Serum samples from rabbits immunized with Test Article #6 from Example 1 were collected at t=0 (P0V) and t=2 weeks (P2Vd14) time points. Pooled, heat inactivated (HI) samples from this group were then tested for neutralizing antibody activity as described below.

Serum samples were diluted 1/6 to 1/96. HFF cells (P=9, used 24 hours post seeded) and TB40-230212 freshly harvested virus were used. TB40-230212 virus is descendant of TB40-010212. TB40-010212 was obtained from ATCC (ATCC VR-1578; Human herpesvirus 5; UL32-EGFP-HCMV-TB40). Virus infection duration was 15 days in a T150 infection flask (Table 2). Microscopic observations indicated the virus was infective. Infection medium was TB40-HFF-1 infection medium (MEM+5% FBS+1% Pen/Strep) or VR1814-APRE-19 infection medium (DMEM:F-12+1% FBS).

TABLE 2

| | | | Virus infection | | |
|---|---|---|---|---|---|
| Virus | Lot# | Ascendant | Duration | Infection flask | Microscope observation |
| TB40 | 230212 | TB40-010212 (new ATCC) | 15 days | T150 | infective |

An HFF seeded T150 flask was infected with CMV TB40-010212 (5 vials)+20 ml of infectious media (MEM—Minimum Essential Medium Eagle from Sigma Cat. No. M4655+5% FBS+1% P/S). After 15 days in $CO_2$ incubator/37° C., the flask was well-infected. Virus was harvested by removing almost the entire supernatant from the flask and keeping sterile in 50 mL Falcon tube. The remaining supernatant, around 5-7 mL, served to help scraping the cells with cell scraper (NUNC, Cat#179707). After scraping, strong pipetting up and down (up to 10×) facilitated virus release from cells. Half of the original supernatant volume from Falcon tube was added (cca. 8 mL) in order to get more potent virus.

Five vials of TB40-010212 (ascendant) from liquid nitrogen was infected in one T150 flask, incubated at 37° C., 5% $CO_2$ for 1 hour. Twelve mL of infection media was added after incubation. Virus was concentrated in 15 mL of supernatant.

Cytogam™ (CMV-IGIV—Cytomegalovirus Immune Globulin Intravenous—Human; CSL Behring; Commercial concentration 2.5 g/50 ml or 50 mg/ml) was used as a positive control. A 1/20 dilution was made as a base concentration (1 in 20 dilution: 100 µL of Cytogam™ 50 mg/mL+1900 µL of infectious media) and later used for making dilutions, the same dilutions used for rabbit sera. Cytogam™ was heat inactivated under the same conditions as rabbit sera (as described in Tables 3-5 below)

TABLE 3

| | Infection Assay | | | |
|---|---|---|---|---|
| Pooled HI P0V | 1/6 | ½ virus | 2 6-well plate wells | 1st plate |
| | 1/12 | ½ virus | 2 6-well plate wells | |
| | 1/24 | ½ virus | 2 6-well plate wells | |
| | 1/48 | ½ virus | 2 6-well plate wells | 2nd plate |
| | 1/96 | ½ virus | 2 6-well plate wells | |
| cells | | | 2 6-well plate wells | |
| Pooled HI P2V | 1/6 | ½ virus | 2 6-well plate wells | 3rd plate |
| | 1/12 | ½ virus | 2 6-well plate wells | |
| | 1/24 | ½ virus | 2 6-well plate wells | |
| | 1/48 | ½ virus | 2 6-well plate wells | 4th plate |
| | 1/96 | ½ virus | 2 6-well plate wells | |
| cells | | | 2 6-well plate wells | |
| HI Cytogam ™ (base 1/20) | 1/6 | ½ virus | 2 6-well plate wells | 5th plate |
| | 1/12 | ½ virus | 2 6-well plate wells | |
| | 1/24 | ½ virus | 2 6-well plate wells | |
| | 1/48 | ½ virus | 2 6-well plate wells | 6th plate |
| | 1/96 | ½ virus | 2 6-well plate wells | |
| TB40-230212 | 1 in 2 diluted | | 2 6-well plate wells | |

TABLE 4

| Pooled sera dilutions for P0V, P2Vd14 and for Cytogam ™ | | | | | | |
|---|---|---|---|---|---|---|
| Used sera dilution | Used sera | Media without FBS to make dilutions (ul) | Total (ul) | Sera used in assay (ul) | Neat virus used in assay (ul) | Final conc. Sera vs. Virus |
| 1/3 | 100 ul neat sera | 200 | 300 | 130 ul 1/3 | 130 | 1/6 vs. ½ |

TABLE 4-continued

Pooled sera dilutions for P0V, P2Vd14 and for Cytogam ™

| Used sera dilution | Used sera | Media without FBS to make dilutions (ul) | Total (ul) | Sera used in assay (ul) | Neat virus used in assay (ul) | Final conc. Sera vs. Virus |
|---|---|---|---|---|---|---|
| 1/6  | 150 ul 1/3  | 150 | 300 | 130 ul 1/6  | 130 | 1/12 vs. 1/2 |
| 1/12 | 150 ul 1/6  | 150 | 300 | 130 ul 1/12 | 130 | 1/24 vs. 1/2 |
| 1/24 | 150 ul 1/12 | 150 | 300 | 130 ul 1/24 | 130 | 1/48 vs. 1/2 |
| 1/48 | 150 ul 1/24 | 150 | 300 | 130 ul 1/48 | 130 | 1/96 vs. 1/2 |

TABLE 5

HFF-1 cell growth and infection media

| | Reagent | Supplier | Cat# | Lot# | Exp | Concentration of components | Volume |
|---|---|---|---|---|---|---|---|
| HFF-1 cells growth media (DMEM + 15% FBS + 1% Pen/Strep) | DMEM (Dulbecco's Modified Eagle Medium) | HyClone | SH30243.01 | AWH17628 | August 2012 | 80% | 420 ml |
| | FBS (Fetal bovine serum) | HyClone | SH30396.03 | AVC67186 | March 2015 | 15% | 75 ml |
| | Pen/Strep (Penicillin Streptomycin Solution) | Sigma | P0781-100 ML | 031M0787 | October 2012 | 1% | 5 ml |
| HFF infection media TB40 (MEM + 5% FBS + 1% Pen/Strep) | MEM (Minimum Essential Medium Eagle) | Sigma | M4655-500 ml | RNC0312 | September 2012 | 94% | 470 ml |
| | FBS (Fetal bovine serum) | Hyclone | SH30396.03 | AVC67186 | March 2015 | 5% | 25 ml |
| | Pen/Strep (Penicillin Streptomycin Solution) | Sigma | P0781-100 ML | 031M0787 | October 2012 | 1% | 5 ml |

Each particular concentration of sera or Cytogam™ and ½ final virus dilution were combined and rotated at 37° C./1 hr. Ready to use 6-well plate with 95%-100% confluent HFF cells were carefully rinsed twice with warm PBS, then virus-sera mixture was applied in duplicate as 100 μL mixture/well+200 μL infection media to avoid drying over 4 hrs. Incubation was at 37° C./5% $CO_2$/4 hrs (rocking was every 60 minutes). After a 4-hour incubation, contents were carefully aspirated from each well with a pipette and 3 mL of fresh infectious media were added. Plates were kept in the incubator at 37° C./5% $CO_2$ for 10 days. Daily checking of virus infection in cells was performed usually after 5 days post-infection. Swelling and rounding cells were visualized by light microscope or green fluorescence detection with a fluorescent microscope.

For sample collection, media was aspirated from each well. Each well was rinsed twice with PBS (HyClone DPBS/modified without Calcium and Magnesium; Cat#SH30028.02) and 100 μL of 1× Trypsin-EDTA (Sigma; Cat#T4174-100 ml) and 100 μL of PBS were added. Samples were kept in $CO_2$ incubator 2-3 minutes until cells were well trypsinized. 1 mL/well of PBS+5% FBS was added to stop trypsin. Samples were collected into transparent flow intended tubes (two wells for same sample/tube) (BD Falcon, 5 ml polystyrene round-bottom, REF 352054). Plates were checked under the light microscope to confirm all cells were collected (if not add additional 500 μL PBS+5% FBS was used to collect the rest). Samples were spun down at 900 rpm for 10 minutes. Supernatant was discarded and the pellet kept. The tube was vortexed so that pellet was dispersed in the leftover buffer. The remaining steps were performed with minimal exposure to light. 200 μL fixative (BD Biosciences, BD Cytofix, Fixation buffer Cat#554655, 100 ml) was added and incubated on ice for 15 minutes. 1 mL/tube of mixture PBS+5% FBS was added to stop Cytofix. Samples were spun down at 900 rpm for 10 minutes. Supernatant was discarded and the pellet kept. The pellet was reconstituted in 500 μL of PBS+5% FBS and vortexed vigorously before putting on flow cytometer.

Samples were subjected to flow cytometry and analyzed using Cellquest software. FSC and SSC parameters were set to "linear", while all other parameters were set to "log."

100,000 cells were collected during flow cytometric analysis of infected cells. Usual conditions for flow using HFF cells and TB40 CMV were FSC E-1 and 4.83; SSC 325; FL1 427, although parameters can be slightly changed around existing conditions in order to get more appropriate dot plot.

Figure 2:
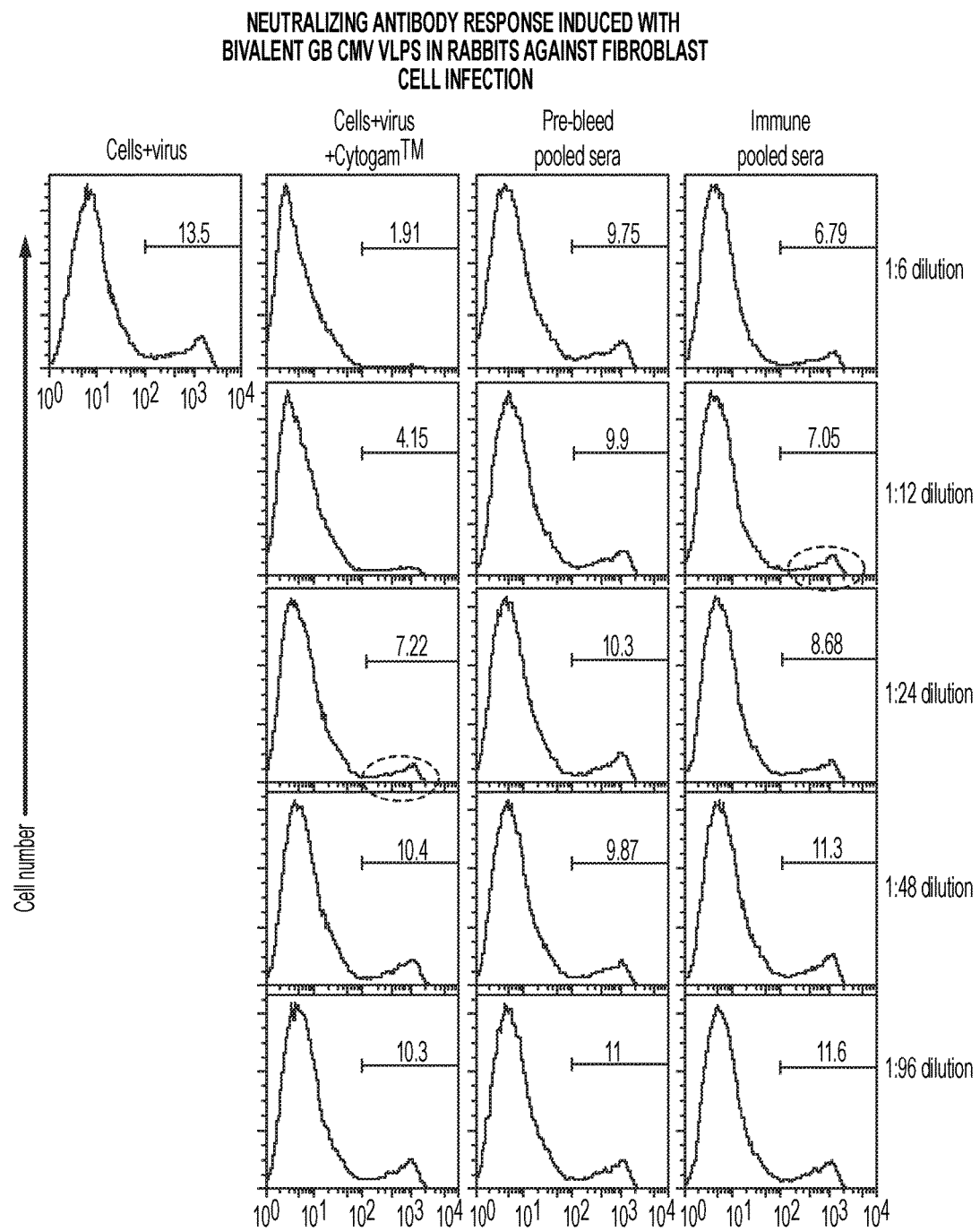
FIG. 2 depicts exemplary FACS analysis of GFP expression in fibroblast cells indicative of neutralizing antibody response induced with gB/pp65 CMV VLPs in rabbits. Rabbits (n=6/group) were immunized (IM) twice at weeks 0 and 8 and bled 2 weeks later. Sera were pooled and tested at indicated dilutions in comparison to Cytogam™ at similar dilutions against GFP-expressing CMV virus (TB40) in HFF fibroblasts. 100,000 cells were collected during flow cytometric analysis of infected (GFP$^+$) cells.

FIG. 2 depicts exemplary FACS analysis of GFP expression in fibroblast cells indicative of neutralizing antibody response induced with gB/pp65 CMV VLPs in rabbits. Rabbits (n=6/group) were immunized (IM) twice at weeks 0 and 8 and bled 2 weeks later. Sera were pooled and tested at indicated dilutions in comparison to Cytogam™ at similar dilutions against GFP-expressing CMV virus (TB40) in HFF fibroblasts. 100,000 cells were collected during flow cytometric analysis of infected (GFP$^+$) cells.

Figure 3:
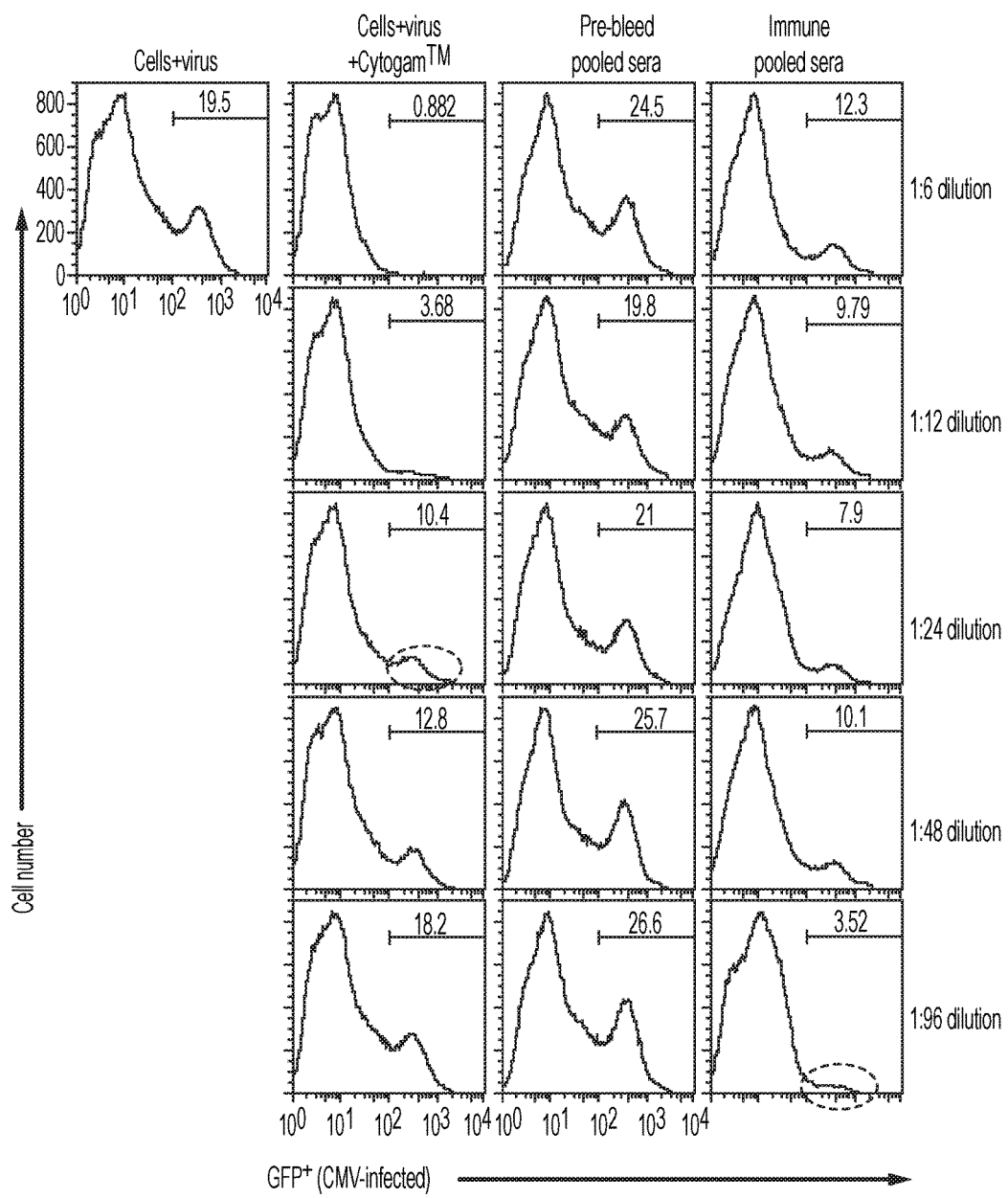
FIG. 3 depicts exemplary FACS analysis of GFP expression in fibroblast cells indicative of neutralizing antibody response induced with bivalent gB+gH CMV VLPs in rabbits. Rabbits (n=6/group) were immunized (IM) twice at weeks 0 and 8 and bled 2 weeks later. Sera were pooled and tested at indicated dilutions in comparison to Cytogam™ at similar dilutions against GFP-expressing CMV virus (TB40) in HFF fibroblasts. 100,000 cells were collected during flow cytometric analysis of infected (GFP$^+$) cells.

FIG. 3 depicts exemplary FACS analysis of GFP expression in fibroblast cells indicative of neutralizing antibody response induced with bivalent gB+gH CMV VLPs in rabbits. Rabbits (n=6/group) were immunized (IM) twice at weeks 0 and 8 and bled 2 weeks later. Sera were pooled and tested at indicated dilutions in comparison to Cytogam™ at similar dilutions against GFP-expressing CMV virus (TB40) in HFF fibroblasts. 100,000 cells were collected during flow cytometric analysis of infected (GFP$^+$) cells.

Example 3: Exemplary Micro-Neutralization Assay for Detection of Neutralizing Antibodies by Flow Cytometry This Example describes detection of functional anti-CMV neutralizing antibodies by flow cytometry in sera samples from vaccinated animals.

Materials/Equipment

The following materials and equipment are used in this assay: Human Foreskin Fibroblasts (HFF-1) cells—ATCC# SCRC-1041; Human Arising Retinal Pigment Epithelia—(ARPE-19)—ATCC#CRL-2302; Human herpesvirus 5 HCMV (UL32-EGFP-HCMV-TB40)—ATCC# VR-1578; Human CMV-GFP-Towne TS15-rR (obtained from Dr. M. McVoy, VCU-Virginia); Goat Antiserum to Rabbit IgG (GAR)—MP Cappel, Cat#: 55620; Complement sera from rabbit—Sigma-Aldrich Cat#57764-5 ml; Standard Guinea pig complement—Cedarlane Cat#CL-5000; Sterile distilled water—Gibco, Cat#15230; Dulbecco's Modified Eagle Medium (DMEM)—HyClone; Cat# SH30243.01 (growth media); Minimum Essential Medium Eagle (MEM)—Sigma; Cat# M4655-500 ml (infectious media); Fetal bovine serum (FBS)—HyClone; Cat# SH30396.03; Penicillin Streptomycin Solution (Pen/Strep)—Sigma; Cat# P0781-100 ml; 1× Trypsin-EDTA—Sigma; Cat#T4174-100 ml; Modified phosphate buffered saline (DPBS—without Calcium and Magnesium)—HyClone; Cat# SH30028.02; Fixation buffer—BD Biosciences; BD Cytofix Cat#554655-100 ml; Cytogam (CMV-IGIV—Cytomegalovirus Immune Globulin Intravenous/human-CSL Behring; Commercial concentration 2.5 g/50 ml; Dimethyl sulfoxide (DMSO)—Sigma-Aldrich Cat# D1435-500 ml; Biosafety cabinet; Incubator 5% CO2, 37° C.; Centrifuge; Vortex; Sample acquisition tubes for a Flow cytometer (BD Falcon, 5 ml polystyrene round-bottom, REF 352054); 6-well plates; Multichannel micropipette reservoirs; 5 and 10 ml graduated pipettes; 10 µl to 1000 µl adjustable single channel micropipettes with disposable tips; Cell scraper—NUNC; Cat#179707; 50 ml Falcon tubes—BD 358206; Rotator—for eppendorf tubes; Fluorescence microscope; FACSCAN machine.

Obtaining and Harvesting the Virus

HFF-1 cells (95% confluent monolayer seeded in T150 flask) are infected with 1.5 ml of UL32-EGFP-HCMV-TB40 ("TB40"). ARPE-19 cells are infected with HCMV-GFP-Towne-TS15-rR ("Towne") in the same manner. Since these viruses are light sensitive, cells are infected with the light off. The flasks are incubated in a CO2 incubator/37° C. for 30 minutes to allow attachment between cells and virus.

25 ml of infectious media is then added to the cells. (see Tables 6 and 7). Flasks are kept in CO2 incubator/37° C. until cells are well infected (in a case of TB40, swelling and rounding cells are seen by light microscope or green fluorescence with fluorescent microscope; for Towne, infection is detected by green fluorescence). Time necessary for good infection depends on the infectious capacity of the ascendant virus.

Harvesting is started by removing almost the entire supernatant from the flask and keeping it sterile in a 50 ml Falcon tube. Residual supernatant, around 5 ml, facilitates scraping of the cells with a cell scraper. Good scraping and strong pipetting up and down (up to 10×) enables virus to release from the cells. 10 ml of the original supernatant volume from the Falcon tube is added and spun down at 900 rpm for 10 minutes. The pellet is removed and around 15 ml of concentrated virus is kept. 5% of cryoprotectant (DMSO) in total amount of virus is added. 1 ml aliquots are prepared, labeled, and kept at −80° C. for short time or in liquid nitrogen for long period of time.

TABLE 6

| HFF-1 cells growth and infection media for CMV-GFP-TB40 | | | | | |
|---|---|---|---|---|---|
| | Reagent | Supplier | Cat# | Concentration of components | Volume |
| HFF-1 growth media (DMEM + 15% FBS + 1% Pen/Strep) | DMEM (Dulbecco's Modified Eagle Medium) | HyClone | SH30243.01 | 80% | 420 ml |
| | FBS (Fetal bovine serum) | Hyclone | SH30396.03 | 15% | 75 ml |
| | Pen/Strep (Penicillin Streptomycin Solution) | Sigma | P0781-100ML | 1% | 5 ml |
| HFF infectious media for CMV-GFP-TB40 virus (MEM + 5% FBS + 1% Pen/Strep) | MEM (Minimum Essential Medium Eagle) | Sigma | M4655-500ml | 94% | 470 ml |
| | FBS (Fetal bovine serum) | Hyclone | SH30396.03 | 5% | 25 ml |
| | Pen/Strep (Penicillin Streptomycin Solution) | Sigma | P0781-100ML | 1% | 5 ml |

TABLE 7

ARPE-19 cells growth & infection media for CMV-GFP-Towne

| | Reagent | Supplier | Cat# | Concentration of components | Volume |
|---|---|---|---|---|---|
| ARPE-19 growth media (DMEM:F-12 + 15% FBS + 1% Pen/Strep) | DMEM:F-12 (Dulbecco's Modified Eagle Medium nutrient mixture F-12 HAM) | HyClone | SH30023.01 | 80% | 420 ml |
| | FBS (Fetal bovine serum) | Hyclone | SH30396.03 | 15% | 75 ml |
| | Pen/Strep (Penicillin Streptomycin Solution) | Sigma | P0781-100ML | 1% | 5 ml |
| ARPE-19 infection media for Towne growth (DMEM:F-12 + 5% FBS + 1% Pen/Strep) | DMEM:F-12 (Dulbecco's Modified Eagle Medium nutrient mixture F-12 HAM) | HyClone | SH30023.01 | 99% | 470 ml |
| | FBS (Fetal bovine serum) | Hyclone | SH30396.03 | 5% | 25 ml |
| | Pen/Strep (Penicillin Streptomycin Solution) | Sigma | P0781-100ML | 1% | 5 ml |

Experimental Set-Up and Method

Pre-bleed and Post-immunized serum samples are heat inactivated at 56° C. for 30 minutes prior to use. Commercial sera, Cytogam, that serves as positive control is heat inactivated, as well. Serum dilutions are made starting from 1/6 up to desired dilutions in duplicates. Cytogam is tested at comparable dilutions, a prior diluting the stock reagent 1:20 to adjust to the Ig content of human/rabbit sera (see Table 8).

TABLE 8

Sera and virus dilutions (as an example 1in2 virus dilution is shown)

| Working sera dilution | Sera volume | Media without FBS to make dilutions (μl) | Total (μl) | Sera volume in assay (μl) | Neat virus in assay (μl) | Final concentration Sera vs. Virus |
|---|---|---|---|---|---|---|
| 1/3 | 100 μl neat sera | 200 | 300 | 130 μl 1/3 | 130 | 1/6 vs. 1/2 |
| 1/6 | 150 μl 1/3 | 150 | 300 | 130 μl 1/6 | 130 | 1/12 vs. 1/2 |
| 1/12 | 150 μl 1/6 | 150 | 300 | 130 μl 1/12 | 130 | 1/24 vs. 1/2 |
| 1/24 | 150 μl 1/12 | 150 | 300 | 130 μl 1/24 | 130 | 1/48 vs. 1/2 |
| 1/48 | 150 μl 1/24 | 150 | 300 | 130 μl 1/48 | 130 | 1/96 vs. 1/2 |
| 1/96 | 150 μl 1/48 | 150 | 300 | 130 μl 1/96 | 130 | 1/192 vs. 1/2 |
| 1/192 (etc.) | 150 μl 1/96 | 150 | 300 | 130 μl 1/192 | 130 | 1/384 vs. 1/2 (etc.) |

Particular concentrations of sera (Cytogam) and virus are combined and rotated at 37° C. for 1 hr. In some assays, complement is included. For assays utilizing complement and HFF cells, 10% standard guinea pig complement is added to each particular sera (Cytogam)/virus mixture. Virus control is treated the same way. For assays utilizing complement and ARPE-19 cells, 2.5% rabbit complement is added to each mix regardless which species is used (rabbit or sera). The sera and virus are rotated at 37° C. for 1 hr.

95% confluent cells (seeded in 6-well plates) are carefully rinsed twice with warm PBS prior to virus-sera mixture application, in duplicate. 100 μl of mixture/well+200 μl infection media is added to avoid drying over 4 hours of incubation. Cells are incubated at 37° C./5% CO2/4 hrs (with rocking every 60 minutes). After a 4-hour incubation, contents from each well are carefully aspirated with a pipette or poured off, and 3 ml of appropriate, fresh, warm infectious media is added. Plates are incubated at 37° C./5% CO2 until well infected. 5 days after incubation, cells are analyzed for virus infection. Infection of HFF-1 cells is determined by swelling and rounding of cells, visualized by light microscope or green fluorescence with a fluorescent microscope. ARPE-19 cell infection is detected as green fluorescence with a fluorescent microscope.

Sample Collection and Preparation for Flow Cytometry

Before sample collection, the presence of good infection is confirmed under a light microscope and, if available, by analyzing GFP integrated into cells using a fluorescent microscope. Media is aspirated or poured off from each well. Cells are rinsed twice with PBS (HyClone DPBS/modified without Calcium and Magnesium; Cat#SH30028.02). To HFF-1 cells are added 100 μl of 1× Trypsin-EDTA (Sigma;

Cat#T4174-100 ml) and 200 μl of PBS. To ARPE-19 cells are added 200 μl of 1× Trypsin-EDTA and 100 μl of PBS. Cells are kept in a CO2 incubator 2-3 minutes until cells are well trypsinized. 1 ml/well of PBS+5% FBS are added to stop trypsin. Cells are collected into transparent flow intended tubes (two wells for same sample/tube) (BD Falcon, 5 ml polystyrene round-bottom, REF 352054). Wells are visualized under a light microscope and if cells remain, an additional 500 μl PBS+5% FBS is added to collect additional cells.

Falcon tubes are spun down at 900 rpm for 10 minutes. The supernatant is discarded and the pellet is kept. The tube is vortexed to disperse the pellet in the residual buffer. The remaining steps are performed in the dark. 200 ul Cytofix (BD Biosciences, BD Cytofix, Fixation buffer Cat#554655 100 ml) are added to each tube and samples are incubated on ice for 15 minutes. 1 ml of mixture PBS+5% FBS is added to each tube to stop Cytofix. Tubes are spun down at 900 rpm for 10 minutes. The supernatant is poured off and the pellet is kept. The pellet is reconstituted in 500 ul of PBS+5% FBS, vortexed vigorously, and flow cytometry is performed.

Example 4: Neutralization Activity of Exemplary VLPs in Rabbits

CHO cells were transfected at a cell density between 1.5E06 to 2.0E06 cells/mL with plasmids of monovalent gB-G and monovalent gH-G (prepared as described in PCT/US2012/64556). Stuffer DNA was added to make total DNA concentration up to 1 μg/mL cell culture. The plasmids used for transfection were first purified by MaxiPrep or GigaPrep plasmid purification kits (Qiagen). The PEIMAX used for transfection to deliver DNA to the cells was provided at a ratio of 6:1 (PEI: DNA wt/wt). The cell culture was harvested 72 hours post transfection by centrifuging at 4000 rpm for 20 minutes, using rotor JS-4.2A by Beckman Coulter, in 1 Liter bottles. The supernatant was filtered through 0.8/0.45 μm filter (AcroPak 500 Capsule, Pall). The filtered supernatant was then concentrated by Tangential Flow Filtration (TFF for concentration of VLPs) and diafiltered against histidine-containing buffer. 704 of Benzonase (Novogen 99% purity (D00127703) containing 250 Units/gL) was suspended in 4004 of PBS that was supplemented with $MgCl_2$ to have a 2 mM final concentration. TFF retentate portions were mixed with diluted Benzonase in PBS solution and kept in a rotary shaker (head-to-toe rotation) at room temperature for 1 hour and then the tubes were placed at 4° C. overnight. The diafiltered benzonase treated material was then loaded onto an anion exchange chromatography column (AEX for reduction of DNA and host proteins) where the flowthrough was collected. The flowthrough was then sterile filtered through 0.45 μm and aliquoted in different volumes.

Monovalent gB-G and monovalent gH-G VLP compositions prepared as described were mixed together, adjuvanted with alum and then tested in female New Zealand White rabbits 6-8 weeks old (minimum 5 animals per test group) for neutralizing activity using the microneutralization assay described in Example 3. Rabbits were immunized intramuscularly with 0.5 ml (250 μl in two sites of the proximal caudal hind thigh muscle) of VLP compositions three times, once on day 0 (Prime) and once on day 57 (week 8 Boost) and once on day 162 (week 24 Boost). Rabbits were treated with 50 μg of both monovalent gB-G and monovalent gH-G (mixed together at a 1:1 ratio) VLP composition. To assess humoral immune responses in rabbits, blood was collected from all rabbits in the study pre-1st immunization and then post-1st immunization days 28, 42 and 55 and post-2nd immunization at day 14.

Neutralizing antibody responses to HCMV were determined using a microneutralization assay in fibroblast cells based on a GFP-expressing CMV virus (TB40) and flow cytometric analysis of infected ($GFP^+$) HFF-1 cells as previously described. Rabbit sera collected pre- and post-immunizations as described were pooled and tested for neutralizing activity in the presence of guinea pig complement against HCMV expressing GFP in HFF fibroblasts relative to a positive control CMV hyperglobulin, Cytogam™ and a negative control consisting of empty Gag VLP (lacking antigenic proteins gB-G and/or gH-G).

Figure 4:
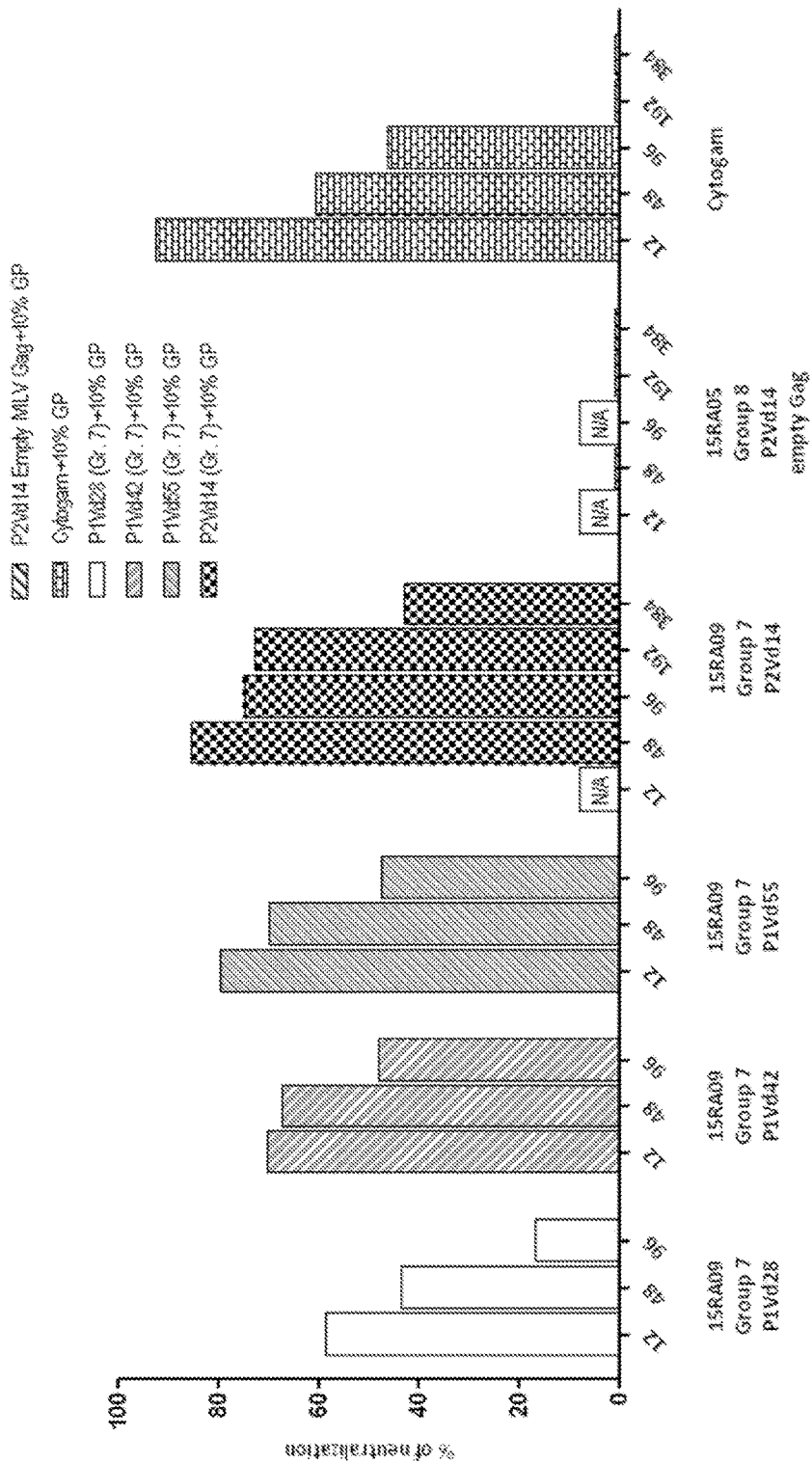
FIG. 4 depicts exemplary percent neutralizations in HFF-1 cells. Depicted are neutralizations for 15RA09 group 7 (monovalent gB-G/monovalent gH-G adjuvanted with alum) pooled samples at P1Vd14, P1Vd28, P1Vd42, P1Vd55, and P2Vd14; and 15RA05 group 8 (empty MLV Gag) at P2Vd14, in presence of 10% guinea pig complement against 1:6 CMV-GFP-TB40-010512 in HFF-1 cells.

FIG. 4 shows the percent neutralization in HFF-1 cells incubated with CMV-GFP-TB40-010512 virus in presence of 10% Guinea Pig complement and rabbit serum (group 7 pooled sera from 15RA09 was used as a positive data representative where animals were treated with monovalent gB-G and monovalent gH-G VLPs three times and also group 8 from 15RA05 study (empty Gag) was used as a negative control representative). As shown in FIG. 4, the combination of monovalent gB-G and monovalent gH-G VLP composition elicited a rapid, synergistic sustained neutralizing antibody response in rabbits against fibroblast cell infection, while the empty Gag VLP showed no neutralizing antibody response. ("GFP-TB40-010512" denotes Human herpesvirus 5 HCMV (UL32-EGFP-HCMV-TB40)—ATCC# VR-1578 (described in Example 3) grown on May 1, 2012.)

Pooled rabbit sera was also tested for neutralizing antibody responses to HCMV using a microneutralization assay in epithelial cells based on a GFP-expressing HCMV virus (Towne TS15-rR) and flow cytometric analysis of infected ($GFP^+$) ARPE-19 cells as previously described. Rabbit sera collected pre- and post-immunizations as described were pooled and tested for neutralizing activity in the presence of 2.5% rabbit complement against HCMV expressing GFP in ARPE-19 epithelial cells relative to a positive control CMV hyperglobulin, Cytogam™ and a negative control consisting of empty Gag VLP (lacking antigenic proteins gB-G and/or gH-G).

Figure 5:
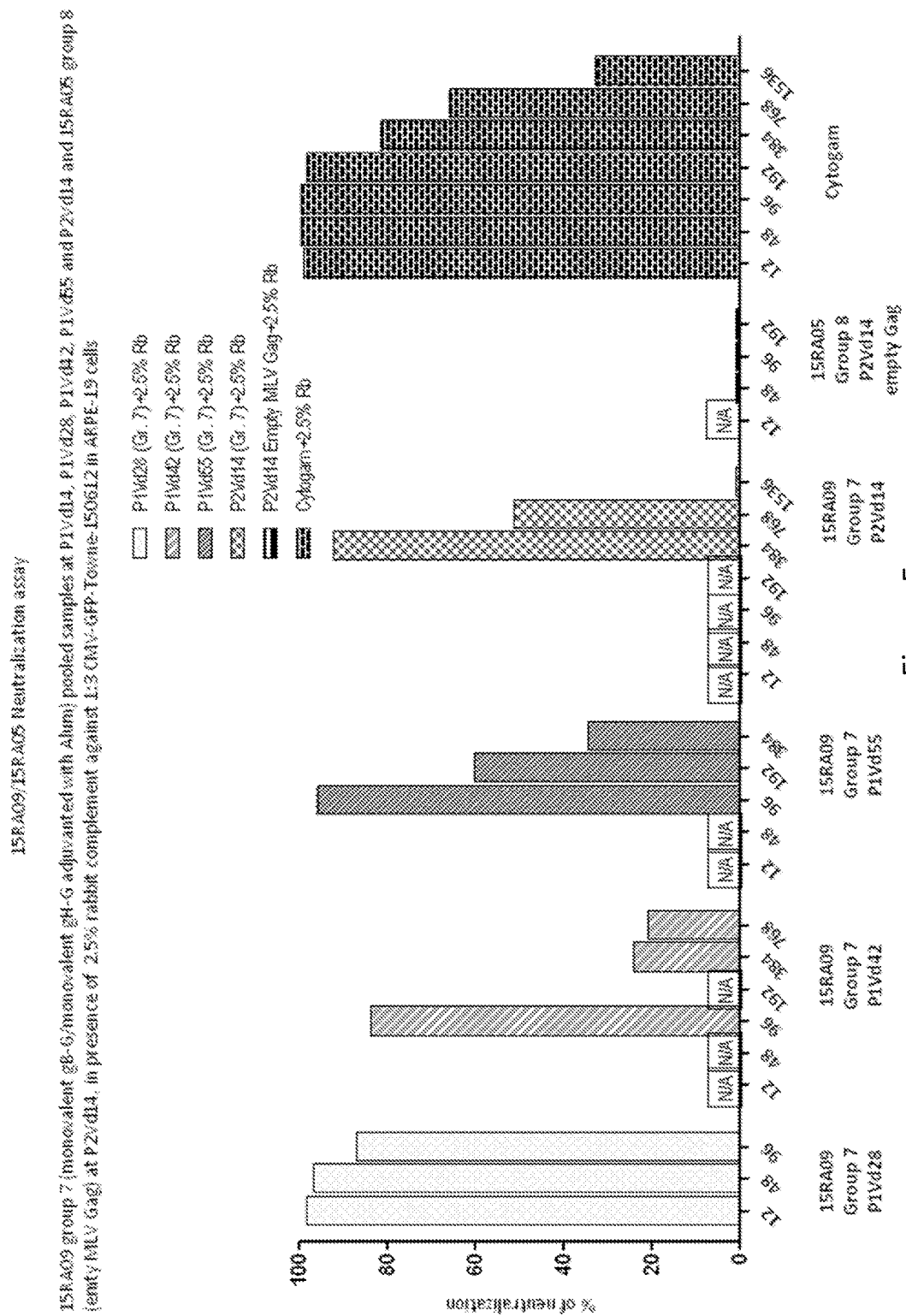
FIG. 5 depicts exemplary percent neutralizations in ARPE-19 cells. Depicted are neutralizations for 15RA09 group 7 (monovalent gB-G/monovalent gH-G adjuvanted with alum) pooled samples at P1Vd14, P1Vd28, P1Vd42, P1Vd55, and P2Vd14; and 15RA05 group 8 (empty MLV Gag) at P2Vd14, in presence of 2.5% rabbit complement against 1:3 CMV-GFP-Towne-150612 in ARPE-19 cells.

FIG. 5 shows the percent neutralization in ARPE-19 cells incubated with CMV-GFP-Towne-150612 virus in presence of 2.5% rabbit complement and rabbit serum (group 7 pooled sera from 15RA09 was used as a positive data representative where animals were treated with monovalent gB-G and monovalent gH-G VLP compositions three times and also group 8 from 15RA05 study (empty Gag) was used as negative control representative). As shown in FIG. 5, the combination of monovalent gB-G and monovalent gH-G VLP composition elicited a rapid, synergistic sustained neutralizing antibody response in rabbits against epithelial cell infection while the empty Gag VLP showed no neutralizing antibody response. ("GFP-Towne-150612" denotes Human CMV-GFP-Towne TS15-rR (obtained from Dr. M. McVoy, VCU-Virginia, and described in Example 3) grown on Jun. 15, 2012.)

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

What is claimed is:

1. A method comprising steps of:
   (i) mixing heat-inactivated serum from a subject that has been immunized with an HCMV candidate vaccine with an HCMV comprising a fluorescent moiety to form a mixture, wherein the HCMV comprising the fluorescent moiety comprises a gH/gL/UL128/UL130/UL131 complex;
   (ii) adding 2.5% rabbit complement to the mixture from (i);
   (iii) contacting a host cell that is susceptible to infection by HCMV, wherein said host cell is a retinal pigmented epithelial cell of cell line ARPE-19, under conditions that allow infection with the mixture of heat-inactivated serum in the presence of rabbit complement of (ii);
   (iv) assessing a fluorescence level of the host cell that has been contacted with the mixture by flow cytometry; and
   (v) determining a level of infection of the host cell based on the assessed fluorescence level.

2. The method of claim 1, wherein the subject that has been immunized is a human.

3. The method of claim 1, wherein the serum comprises anti-HCMV neutralizing antibodies.

4. The method of claim 1, wherein the HCMV candidate vaccine comprises VLPs.

5. The method of claim 4, wherein the VLPs comprise one or more of gB, gH, and pp65 from HCMV.

6. The method of claim 1, wherein the mixture of (ii) is incubated for at least 15 minutes, at least 30 minutes, at least 1 hour, or at least 2 hours before step (iii).

7. The method of claim 1, wherein the assessing step (iv) is performed in a high throughput manner.

8. The method of claim 1, wherein the assessing step (iv) comprises comparing the fluorescence level to a reference.

9. The method of claim 8, wherein the reference is a historical reference.

10. The method of claim 8, wherein the reference is a side-by-side reference.

11. The method of claim 1, further comprising determining an anti-HCMV neutralizing antibody titer in the serum based on the determining step.

12. The method of claim 11, further comprising evaluating the efficacy of the candidate HCMV vaccine based on the determining step.

13. The method of claim 12, further comprising selecting the candidate HCMV vaccine as a vaccine that induces neutralizing antibodies if the fluorescence level of the host cell that has been contacted with the mixture is lower than a reference fluorescence level.

14. The method of claim 1, wherein the contacting step (iii) comprises an incubation of at least 1 hour, at least 2 hours, at least 3 hours, at least 4 hours, at least 5 hours, at least 6 hours, at least 7 hours, or at least 8 hours.

15. The method of claim 1, wherein the host cell is further monitored for infection by visual cellular morphology assessment or visual fluorescence assessment.

16. The method of claim 15, wherein the visual cellular morphology assessment comprises monitoring for cellular swelling and rounding.

17. The method of claim 15, wherein the visual fluorescence assessment comprises detecting fluorescence.

18. The method of claim 17, wherein the fluorescence is detected on a fluorescence microscope.

19. The method of claim 1, wherein a fluorescence level of the nucleus of the host cell is assessed.

20. The method of claim 1, wherein a fluorescence level of the whole host cell is assessed.

21. The method of claim 1, further comprising a step of quantitating the fluorescence level of the host cell.

* * * * *